United States Patent [19]

Clanton et al.

[11] Patent Number: 4,665,917

[45] Date of Patent: May 19, 1987

[54] TISSUE GRIPPER FOR USE WITH INTRALUMINAL STAPLING DEVICE

[75] Inventors: Marlene K. Clanton, Somerville, N.J.; Jeffrey Kapec, Westport; Kanuza Tanaka, Cos Cob, both of Conn.

[73] Assignee: Ethicon, Inc., Somerville, N.J.

[21] Appl. No.: 791,029

[22] Filed: Oct. 24, 1985

Related U.S. Application Data

[62] Division of Ser. No. 695,709, Jan. 28, 1985, abandoned.

[51] Int. Cl.[4] .............................................. A61B 17/04
[52] U.S. Cl. .................................. 128/334 R; 128/346
[58] Field of Search ............... 128/334 R, 335, 303 R, 128/337, 346, 303

[56] References Cited

U.S. PATENT DOCUMENTS

| | | | |
|---|---|---|---|
| 1,151,300 | 8/1915 | Soresi | 128/335 |
| 3,357,432 | 12/1967 | Sparks | 128/335 |
| 4,351,466 | 9/1982 | Noiles | 128/334 R |

FOREIGN PATENT DOCUMENTS 0158316  10/1985  European Pat. Off. ........ 128/334 C

*Primary Examiner*—Richard C. Pinkham
*Assistant Examiner*—Gary Jackson
*Attorney, Agent, or Firm*—Robert L. Minier

[57] ABSTRACT

The improvement in an intraluminal stapling instrument comprising a clamping means disposed on the central member of said instrument. The clamping means holds the tissue to be joined in the proper position with respect the fasteners being used to accomplish the fastening.

2 Claims, 5 Drawing Figures

4,665,917

TISSUE GRIPPER FOR USE WITH INTRALUMINAL STAPLING DEVICE

This is a division of application Ser. No. 695,709 filed Jan. 28, 1985, now abandoned.

The present invention relates to a tissue gripper for use with intraluminal stapling devices.

BACKGROUND OF THE INVENTION

In recent years there have been developed a number of instruments for placing fasteners in a circular configuration or in a plurality of circular configurations for use in reconnecting severed hollow organs. These devices are used to perform anastomosis; that is, join the cut end of hollow organs or vessels. Whenever the term "vessel" is used throughout this specification it means any hollow tubular organ; such as, intestine, blood vessel, esophagus etc.

Generally speaking, these intraluminal stapling devices comprise a centrally extending longitudinal member on which there is mounted a circular anvil member and a circular staple holding member. These members are separated from one another but are movable along the centrally located member so that they may be placed adjacent each other. To join a severed vessel, one end of the severed vessel is pulled over the anvil portion of the intraluminal device. A purse string suture; that is, a loosely placed suture, is placed around the cut end of the vessel in a manner to act as a purse string so that it may be pulled tight and pulls the loose end of the vessel down tightly about the centrally located member with portions of the vessel or the tissue then disposed directly underneath the anvil of the instrument. The opposite end of the vessel to be joined is pulled over the stapling portion of the instrument in a similar manner. It is also pulled down utilizing a purse string suture so that it is tied against the centrally located member of the instrument and the tissue underlies the staple applying member. At this point, the staple and anvil are moved towards one another to provide a correct gap between the tissues to be joined. Once that correct gap is obtained, the staples are fired, joining the vessel. Staples may be disposed in various arrays, although usually a pair of concentric circles with the staples offset in adjacent circles is used. Once the staples have been fired, a circular knife, which has a smaller diameter than the smallest array of staples that have been fired, severs the tissue inside the staple line and outside the purse string sutures. The anvil and staple holder may then be backed off or separated and the instrument carefully removed from the rejoined vessel. An example of such an instrument is more fully disclosed in U.S. Pat. No. 4,351,466, issued Sept. 28, 1982.

As can be appreciated from the above description, a critical point in the procedure is to be sure the tissue is positioned up against the central longitudinal extending member of the instrument so that the tissue underlies those portions of the instrument which are used to join the tissue together. Depending on the location of the vessel, size of the vessel, etc., it is often very difficult, if not virtually impossible, to place a suitable purse string suture in a manner so as to insure good juxtaposition of the vessels.

It is an object of the present invention to provide a simple means for gathering the open end of the vessel. It is a further object of the present invention to provide a means which insures that the open end of a vessel can be positioned or juxtaposed correctly with respect to a fastening member of an intraluminal device. It is a further object of the present invention to provide means which can readily position the open end of a vessel to be joined simply, and even in the most difficult positions in which to work.

SUMMARY OF THE PRESENT INVENTION

What we have discovered is an improvement to an intraluminal stapling instrument used to join the open ends of vessels. Such an instrument generally comprises a central longitudinally extending member. Disposed on the central longitudinally extending member are a pair of fastening means. At least one of said fastening means is slidably movable toward and away from the other along the central member. One of the fastening means carries fasteners while the other fastening means is an anvil for crimping the fasteners or otherwise securing the fasteners in place once they are set. It is preferred that the anvil fastening means be slidably movable. In use the instrument is placed within the lumen of the vessel to be joined. One of the fastening means carries a circular array of fasteners disposed about the central member. The fasteners are used to join together and hold the joined vessels together. Our improvement comprises clamping means cooperating with the central member to grasp the open end of the vessel to be joined and hold the vessel in position adjacent the central member. Our clamping means positions the open end of the vessel beneath the circular array of fasteners whereby when the intraluminal stapling device is actuated, the fasteners engage the vessel adjacent the open end of the vessel. In certain embodiments of the present invention, an clamping means comprises a circular clamp. The clamp preferably comprises two sections hingedly connected to each other at one end thereof and open at the other end thereof. The inside surface of the clamp includes gripping means such as pins. The open end of the clamp may also include a locking feature and preferably an adjustable locking feature. In use, an open end of the vessel to be joined is placed over the slideably movable means of the intraluminal stapling instrument and the clamp placed over the end of the vessel to be joined with the hinge of the clamp in an open position. The open ends of the clamp are brought together causing the clamping means to grasp the vessel and as the clamp is closed the vessel is constricted about the central longitudinally extending member of the intraluminal device to cause the tissue to be positioned underneath or juxtapositioned correctly with respect to the fastening means carrying the circular array of fasteners. In other embodiments of the present invention the clamping device may comprise a plurality of pins or hooks extending radially from the central longitudinally extending member of the intraluminal stapling instrument. In use, when the open end of the vessel is placed over the slideably movable means of the instrument, the open end of the vessel is connected to the hooks utilizing forceps to correctly juxtaposition the vessel with regard to the fasteners. As can be appreciated one clamping device may be used to grasp both ends of the vessel to be joined or separate clamping devices may be used or in some instances it may even be desirable to use a clamping device on one end of the vessel to be joined and a purse string suture on the opposite end.

BRIEF DESCRIPTION OF THE DRAWINGS

The invention will be more fully described in conjunction with the accompanying drawings wherein.

DETAILED DESCRIPTION OF THE DRAWINGS

Figure 1:
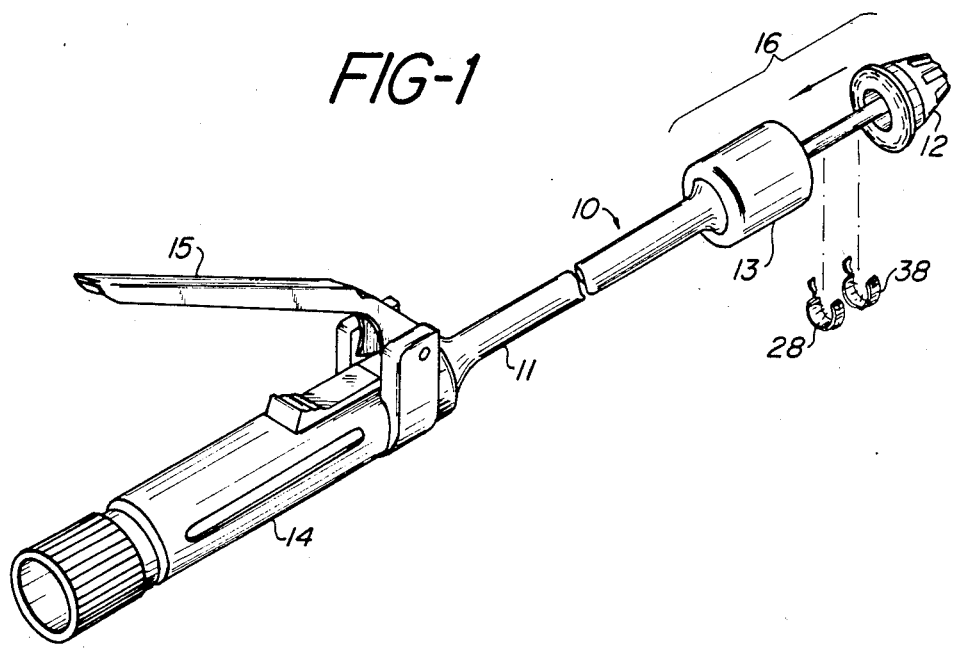
FIG. 1 is a perspective view of one type of intraluminal stapling instrument with which the improvement of the present invention may be used.

Referring to the drawings, in FIG. 1 there is shown a perspective view of an intraluminal stapling instrument 10 which may be used with the improvement of the present invention. The intraluminal stapling instruments comprise a centrally disposed longitudinally extending member 11. Disposed at one end of the central member is a movable anvil 12 and spaced a distance from the anvil is a fastening member 13 carrying suitable tissue fasteners. At the opposite end of the central longitudinally extending member is means 14 for controlling the distance between the slideably movable anvil and the fastening means 13. Also disposed at the same end is means 15 for firing the fasteners carried by the fastening member 13. In use, the operating end 16 of the instruments is passed entirely through one end of the vessel to be joined. The other portion of the vessel to be joined is slipped over the anvil and in prior instrument the vessel tied via a purse string suture down about the centrally extending longitudinal member. In the prior art the open end of the vessel through which the instrument is passed is also tied using a purse string suture about the centrally extending longitudinal member and adjacent the fastening member. The knob 14 at the control end of the instrument is turned to bring the fastening member and the anvil to the correct gap for joining tissue. At this point, the firing means 15 is actuated and the fasteners placed in the tissue. A circular knife is actuated to cut the tissue within the circular array of fasteners. At this point, the knob at the control end is backed off separating the anvil and the fastening member and the instrument gently removed from the reconnected vessel.

Figure 2:
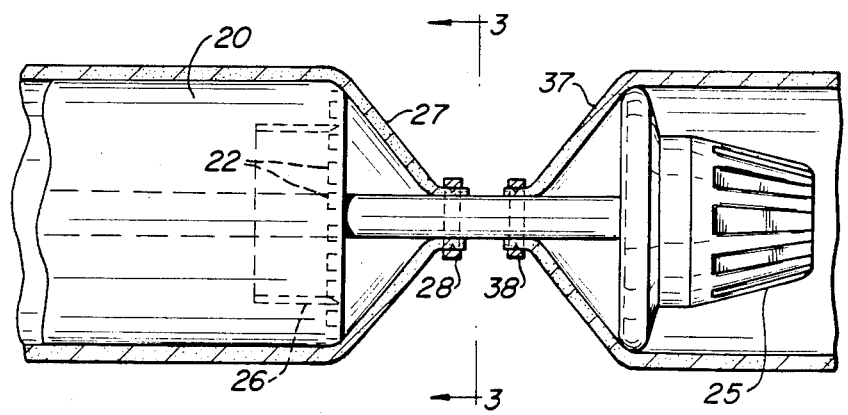
FIG. 2 is a cross-sectional view of an intraluminal stapling instrument depicting the improvement of the present invention clamping the vessels to be joined in place.
Figure 3:
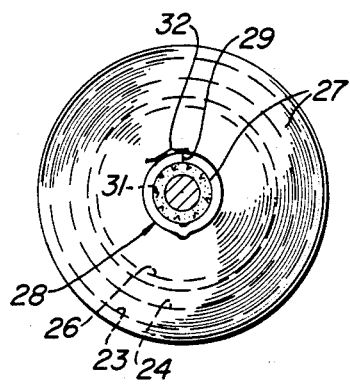
FIG. 3 is a view taken along line 3—3 of FIG. 2 with certain portions of the vessel removed.
Figure 4:
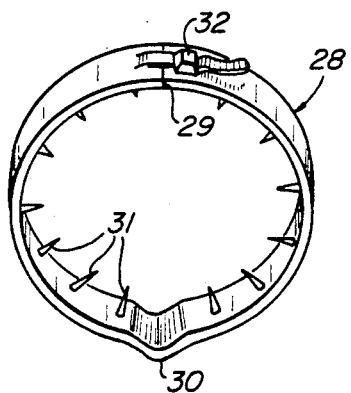
FIG. 4 is a perspective view of one type of clamping device of the present invention.

As may be more clearly seen in FIGS. 2 and 3, the instrument has a fastening member 20. One end of the member 20 carries a plurality of fasteners 22, in this instance, metal fasteners, and these metal fasteners are disposed in two circular arrays 23 and 24 of fasteners with the fasteners offset in the arrays. The anvil 25 is movable with respect to member 20. The fastening member 20 also carries a circular knife 26 which is disposed within the inner circular array of fasteners. The fastening member carries suitable pushers and a suitable actuator (not shown) as is well known in the art for actuating both the fasteners and the knife once the fastening member and the anvil are correctly spaced to join the desired tissue. One end 27 of the vessel to be joined is positioned over the fastening member while the opposite end 37 of the vessel to be joined is positioned over the anvil. The end 27 of the vessel is clamped about the centrally located member by a clamp 28 more clearly shown in FIG. 4. The clamp is circular and has an open portion 29 or a split at one point along its periphery. Substantially directly opposite the split is a hinge 30. If desired the clamp could be in two parts but a single hinged piece is usually easier to apply. The inside surface of the clamp contains a plurality of barbs or needles 31. The outer surface of the clamp at the split portion also includes a suitable locking mechanism 32 which is preferably adjustable and in this instance is merely a ratchet mechanism which is disposed on one side of the split and an appropriate grasping mechanism disposed on the opposite side of the split. In use, the clamp 28 is merely placed over the open end of the vessel 27 and about the central member. The clamp is closed and locked to constrict the open end of the vessel about the central longitudinally extending member. A similar clamp 38 is used to constrict the open end of the vessel 37 about the anvil 25. The anvil is moved to the fastening member and the appropriate gap set. The fasteners are placed and the knife actuated. The anvil is backed off and the instrument removed. The clamps may be made from either metal or polymeric material or similar materials as desired.

Figure 5:
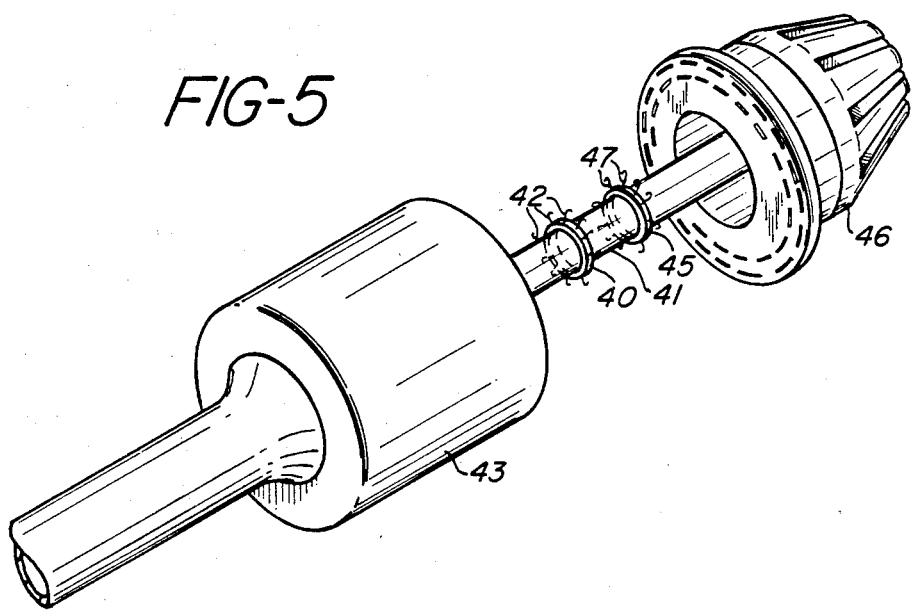
FIG. 5 is an enlarged perspective view of the end portion of an intraluminal stapling instrument showing another type of clamping device of the present invention positioned on said instrument.

In FIG. 5 there is shown another embodiment of the clamping device of the present invention. In this embodiment the clamp 40 is a ring or collar disposed on the central longitudinally extending member 41 of an intraluminal stapling instrument. Disposed outwardly from the surface of the clamps are a plurality of pins or hooks 42. The open end of the vessel to be joined is brought over the fastening member 43 using forceps and is engaged by the pins 42. A second similar clamp 45 is disposed adjacent the anvil 46 of the instrument. The opposite end of the vessel to be joined is brought over the anvil using forceps and engaged by the hooks 47 of the clamp. The clamps are slidably movable along the member 41 and in a preferred embodiment portions of the fastening member 43 and the anvil 46 adjacent the central member 41 are undercut to allow the fastening member to be brought adjacent the anvil to the required tissue gap and the fasteners then fired to join the vessel.

In certain embodiments, the pins of the clamp may be made from heat shape memory material such as Nitinol or similar alloys so that the pins may have one configuration when the tissue is impaled on the pins and then the pins deformed by heat to take another configuration. The new configuration would be such that the hook grasp the tissue and bring it down about the central longitudinally extending member.

Though we have described utilizing two clamps for joining both the proximal and the distal ends of the vessel, in certain procedures it may be that only one clamp is required. Also in some procedures one clamp may be used for one end of the vessel while the opposite end of the vessel is placed utilizing a purse string suture.

Having now described the invention, it should be readily apparent that many variations and modifications may be made without departing from the spirit and scope of our invention.

What is claimed is:

1. In an intraluminal stapling instrument for joining hollow tubular organs, said instrument including a central longitudinally extending member, means disposed on said member for placement within the lumen of a hollow tubular organ to be joined, said means adapted to carry a circular array of fasteners disposed about said central member for joining together and holding the joined hollow tubular organ, the improvement comprising:

clamping means slidably disposed on said central longitudinal extending member, said clamping means comprising a circular array of barbs extending outwardly from the central longitudinally extending member to grasp the open end of the hollow tubular organ to be joined and hold said organ in a constricted position adjacent the central member and beneath the circular array of fasteners whereby when said instrument is actuated, said fasteners are caused to engage the hollow tubular organ adjacent the open end thereof.

2. The improvement according to claim 1 wherein there are two circular arrays of barbs on said longitudinally extending member.

* * * * *